119/1

United States Patent [19]
Gruss

[11] 4,326,481
[45] Apr. 27, 1982

[54] URINE COLLECTION PROCEDURE FOR CATS AND APPARATUS THEREFOR

[76] Inventor: John E. Gruss, Burke, Va.

[21] Appl. No.: 203,482

[22] Filed: Nov. 3, 1980

[51] Int. Cl.³ .............................................. A01K 29/00
[52] U.S. Cl. ...................................................... 119/1
[58] Field of Search ................................ 119/1, 17, 15

[56] References Cited

U.S. PATENT DOCUMENTS

| | | | |
|---|---|---|---|
| 2,971,493 | 2/1961 | Robb | 119/1 |
| 3,107,650 | 10/1963 | Cass | 119/17 |
| 3,225,738 | 12/1965 | Palencie | 119/17 |
| 3,429,297 | 2/1969 | Schroer | 119/17 |
| 3,476,083 | 11/1969 | Vander Wall | 119/1 |
| 3,886,901 | 6/1975 | Zeitter | 119/1 |
| 3,965,863 | 6/1976 | Scott | 119/1 |

*Primary Examiner*—Jay N. Eskovitz
*Attorney, Agent, or Firm*—Abraham A. Saffitz

[57] ABSTRACT

Smooth plastic or rubber granular material is used as an aid in taking a urine sample from a cat or a member of the cat family. The urine sample is necessary in order to carry out a complete physical examination in veterinary medicine and is of special importance in diagnosing disorders of the urinary tract. Novel apparatus is also provided for use with the granular material to aid in obtaining the urine sample without the need for manual expression of the bladder, cystocentesis or confinement of the cat within a special rack in the veterinarian's quarters or in an animal hospital.

16 Claims, 18 Drawing Figures

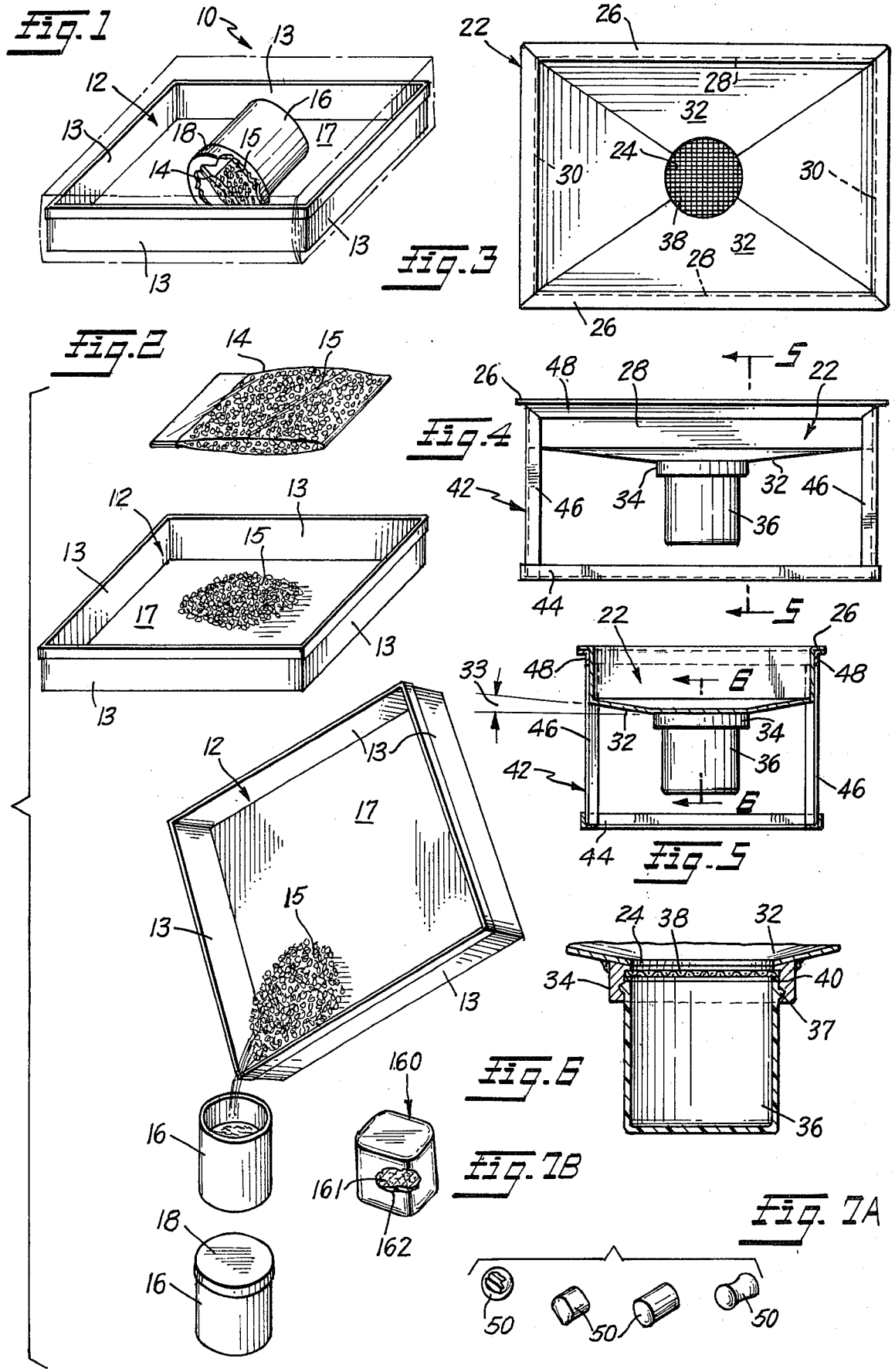

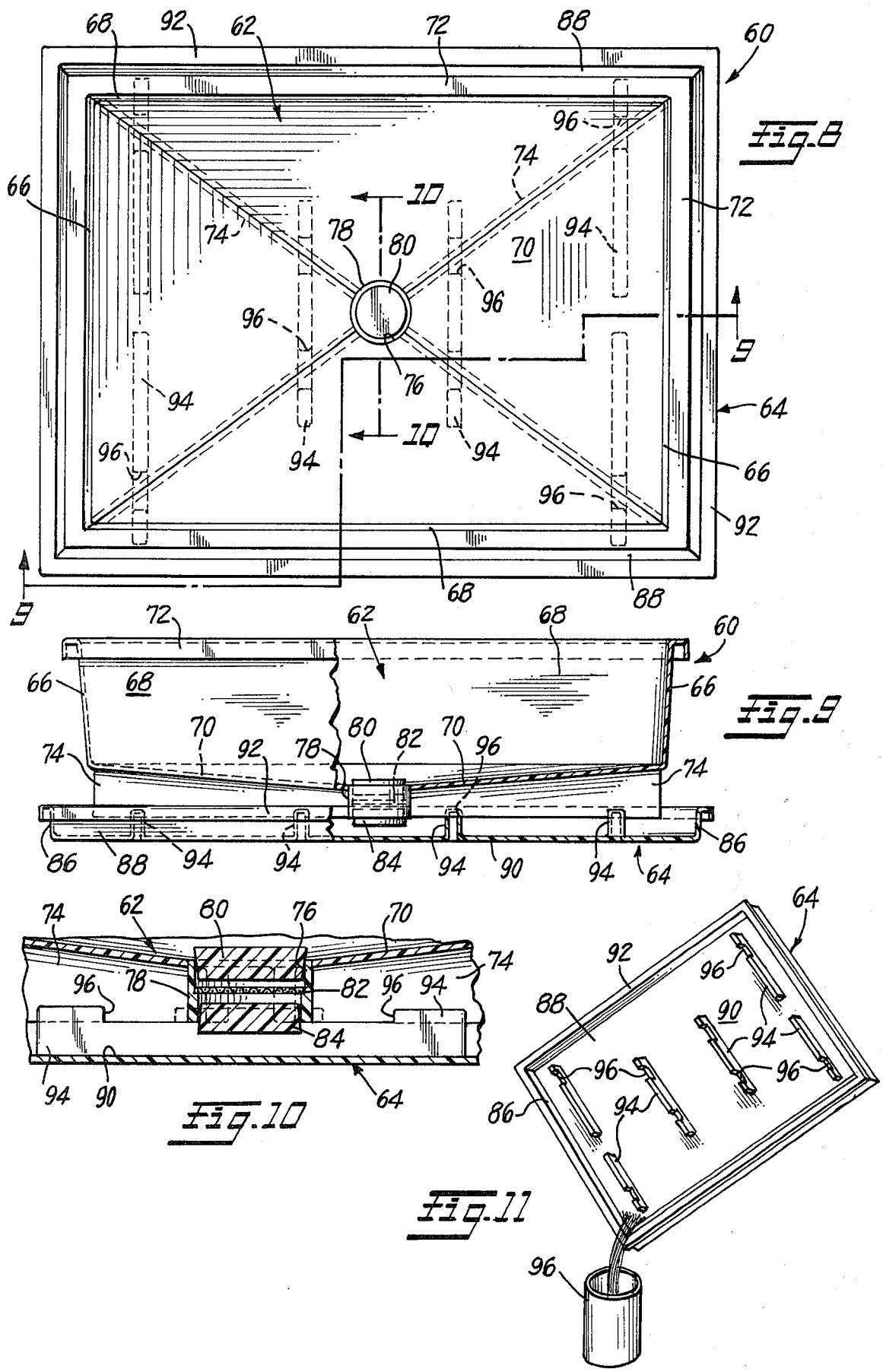

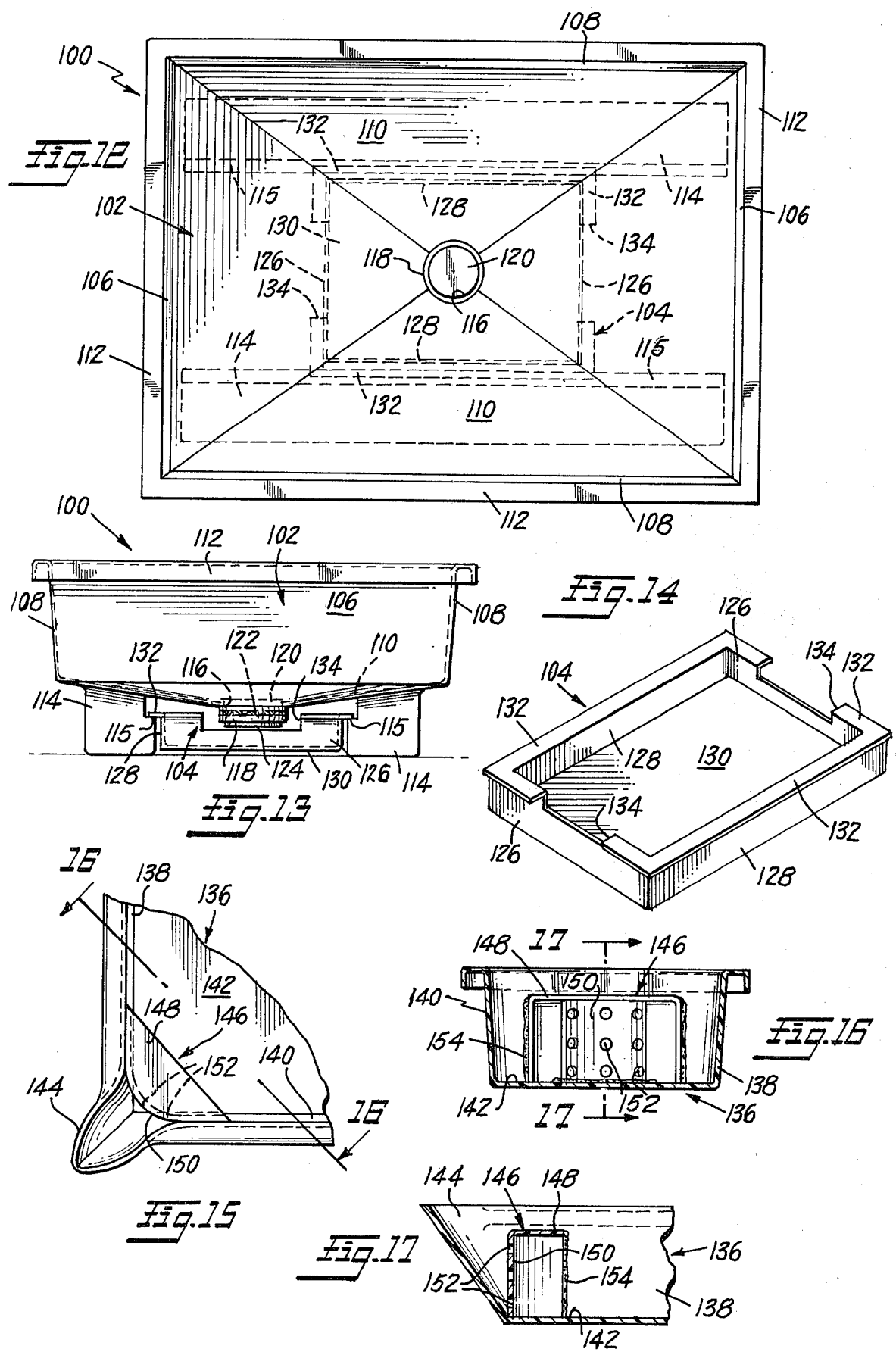

URINE COLLECTION PROCEDURE FOR CATS AND APPARATUS THEREFOR

BACKGROUND OF THE INVENTION

FIELD OF THE INVENTION

This invention lies in the field of veterinary medicine and cat husbandry and in particular in the field of improving apparatus and procedures for the taking of urine samples from the cat and members of the cat family.

DESCRIPTION OF THE PRIOR ART (a) Prior Procedures For Sampling

The taking of sample of urine from a cat or a member of the cat family frequently presents a problem in veterinary medicine especially since these animals are prone to disorders of the urinary tract.

Current methods include:

1. Cystocentesis: This is the only method available to obtain a sterile sample. The skin is surgically prepared (shaved), the bladder is isolated by palpation, and a needle is passed through the skin and into the bladder. The urine is then aspirated into a sterile syringe. A sterile sample, however, is seldom required. The preparation cost and risk to the animal also are disadvantages of this method.

2. Manual expression of the bladder: This empties the bladder by applying pressure around the bladder. This is often not productive. It also is potentially hazardous to the animal as excessive pressure may cause the bladder to rupture. Also, by compressing the bladder, cells, debris and blood may be dislodged from the bladder wall which make interpretation of the sample difficult.

3. Catheterization: This is the method in which a catheter is passed through the urethra and into the bladder. It is often difficult to perform in both male and female cats without anesthetic. It is also easy with this method to bruise or even rupture the urethra or bladder. This method can also be time consuming and is sometimes economically prohibitive.

4. Confinement of the cat in a cage with a rack: The principle is that the cat will urinate in the cage. The cat sits on a metal rack that allows the urine to pass into a pan for collection. Cats, however, are usually reluctant to urinate on the rack and will often retain urine for twenty-four hours or even longer. This presents several problems. First, this retention of urine is not healthy for the cat. Second, it delays the diagnosis if the cat does have a urinary tract infection, and thus delays treatment. Third, cost to the client increases each day the cat remains in the hospital. Fourth, debris may settle in the collection pan and alter the results of the urinalysis.

None of the foregoing procedures are satisfactory for reasons stated above and there is a real need for a procedure which can be carried out with the help of the cat owner to cut down on the expense, time, and handling hazard in attempting to obtain a sample of urine without being scratched or bitten by the cat or member of the cat family suspected of having a urinary disorder.

(b) Prior Art Patents Of Interest To The Invention

Pallesi U.S. Pat. No. 3,752,120 granted Aug. 14, 1973, discloses a litter box for use by cats employing a series of three nesting containers, one filled with sand, one having a wire screen bottom, and the third being formed with a solid bottom like the first. The litter box of this invention is arranged with screen bottom at the top and the other two containers with solid bottoms fitting at the bottom so that after use the sand from the top container pours into one of the bottom containers. This permits the series of containers to be readily cleaned of refuse. This also permits the sand to be washed and re-used. Obviously, this system cannot be used to obtain a representative urine sample from a cat or a member of the cat family due to the absorbency of the sand.

Fisher U.S. Pat. No. 3,765,371 granted Oct. 16, 1973, discloses a system for animal excrement control which comprises the use of foamed plastics or foamed synthetic rubbers especially formulated by the method of preparation to be highly adsorbent. These absorbent plastic or rubber plastics are impregnated with bactercide, antioxidant, deodorizer and surfactant to eliminate the odor, bacterial growth, etc., of the urine or other excrement. Accordingly, these additives prevent the Fisher material from possible use as an aid in taking a sample of urine.

Janecek U.S. Pat. No. 4,047,499 granted Sept. 13, 1977, discloses a pet waste disposal pan having a planar rectangular base, shallow walls, and a notched intermediate portion of two of the walls which adapts the pan to be folded and form a pouring channel. No additional material is added to aid the animal in urinating.

Edgar U.S. Pat. No. 4,164,314 granted Aug. 14, 1979, describes a single use package for cat litter which is made of the usual granular absorbent clay material (see column 1, line 46-50) to which is added an odor depressant material which will absorb urine and minimize odor. This conventional litter material prevents a meaningful sample of urine from being obtained therefrom.

OBJECTS OF THE INVENTION

An object of the invention is to provide a non-absorbent and non-porous, non-adsorbent substantially smooth, granular, hydrophobic plastic or rubber or equivalent material of specified particle size to aid in taking a urine sample from a cat or a member of the cat family.

A further object of the invention is to provide novel apparatus to aid the cat owner, the veterinary technician and the doctor of veterinary medicine to collect a sample of urine from a cat or a member of the cat family.

Other and further objects will be apparent from the accompanying drawings, the following detailed descriptions and the claims.

SUMMARY OF THE INVENTION

It has been discovered that a smooth plastic or rubber non-absorbent granular material in a particle size of 1-2 millimeters up to about 10 millimeters provides a minimum loss of urine when used as a litter in a pan, this granular size and consistency being acceptable to cats and members of the cat family when used in relatively small quantities as the sole litter in a pan in which the urine is to be collected.

Contrary to the absorbency encountered with conventional clay particles which are absorbent or sand which has been used as litter heretofor, the particle size consistency, smoothness and lightness in weight of these non-absorbent particles of rubber or plastic make the urine separation from these granules very easy and highly efficient yet completely acceptable to the cat in its normal excretory activities.

Preferred smooth plastic or rubber granular material used as an aid in taking a urine sample include synthetic plastics or synthetic rubber which have a low density and are low in cost. Those synthetic plastics which are very hard, such as highly cured phenol-formaldehyde resin which fractures to provide sharp edges is less preferred because it can cause damage to the animal. Molded thermoset plastic particles, such as melamine resin may be used. High density plastics, such as vinyl chloride, chlorotrifluoroethylene plastics are more expensive, more difficult to work with, and do not have the desirable lightness properties of such light weight vinyl plastics, such as polyethylene, polypropylene, polybutadiene, polystyrene, etc. Vinyl polymers and copolymers which are shown in the text "Vinyl and Related Polymers" by Calvin E. Schildknecht are preferred. The preferred family of these vinyl type polymers of low density are illustrated in this book in the chart opposite the title page, the book being published by John Wiley and Sons, copyright 1952.

The plastic is preferably pigmented in a dark color, black, dark brown, umber or shades of earth colors which appear to be acceptable to the cat. Other colors, white, red, yellow and blue have been used but it is believed that a preference exists for the darker colors of non-absorbent plastic material.

The urine collecting system of the invention may be carried out in an ordinary pan adapted for conventional litter or the special granular material of the invention or in a third embodiment in a novel special pan apparatus with the litter of the invention which is adapted to be used to drain the sample into a urine receiving container. Various embodiments of the special novel pan apparatus are provided.

BRIEF DESCRIPTION OF THE DRAWING

FIG. 1 is a perspective view of a packaged kit containing the components for collecting a sample of the urine of a cat according to the present invention, the outline of the package being shown in phantom line for purposes of illustration;

FIG. 2 is an exploded view in perspective of the components of the kit of FIG. 1 showing the procedure for collecting the urine;

FIG. 3 is a plan view of a first modification of the collecting tray;

FIG. 4 is a side elevational view of the first modification of the collecting tray of FIG. 3 and its associated support;

FIG. 5 is a transverse sectional view, taken on the line 5—5 of FIG. 4;

FIG. 6 is an enlarged vertical sectional view, through the urine receiving container, taken on the line 6—6 of FIG. 5;

FIG. 7A is an enlarged perspective view of various shapes for the non-absorbent litter granules made from extruded plastic or rubber;

FIG. 7B is an enlarged perspective view of a modification of a litter granule to show non-absorbent litter prepared by coating non-plastic material with plastic or rubber;

FIG. 8 is a plan view of a second modification of a litter pan and a urine receptacle;

FIG. 9 is a side elevation of the litter pan and urine receptacle, partly in section, taken on the staggered line 9—9 of FIG. 8;

FIG. 10 is an enlarged fragmentary vertical sectional view, taken on the line 10—10 of FIG. 9;

FIG. 11 is a perspective view of the urine receptacle removed from the litter pan showing the urine specimen being poured into a container;

FIG. 12 is a plan view of a third modification of the litter pan and urine receptacle;

FIG. 13 is an end elevational view as seen from the right of FIG. 12;

FIG. 14 is an isometric view of the urine receptacle of FIGS. 12 and 13;

FIG. 15 is a fragmentary plan view of a fourth modification of the litter pan having a pouring spout at one corner thereof;

FIG. 16 is a fragmentary transverse vertical sectional view, taken on the line 16—16 of FIG. 15; and FIG. 17 is a fragmentary vertical sectional view through the pouring spout and strainer, taken on the line 17—17 of FIG. 6.

DESCRIPTION OF THE PREFERRED EMBODIMENTS

FIGS. 1 and 2 illustrate the novel components of a package 10 to aid in urine collection, these comprising packaged litter 15 in a flexible pouch 14, a tray 12 having side walls 13 and a bottom wall 17. The package 10 also includes a collection container 16 having a lid 18. The urine is taken from a cat in its normal function as a result of spreading the litter contents in the conventional rectangular tray 12 and pouring the urine from tray 12 away from the litter into container 16. Smooth non-absorbent particles of plastic or rubber, which are of substantially uniform particle size, preferably one to two millimeters in the smaller dimension and up to five millimeters in size as a maximum (about twice the minimum for the maximum particle size) constitute the essential litter material in the urine collection system of the present invention. FIGS. 7A and 7B show various shapes of litter.

The novel method and apparatus of the invention which is provided by the preferred granular material illustrated in FIGS. 1, 2, 7A and 7B have the following advantages:

1. The granular consistency is more acceptable to cats, and simulates a material they are accustomed to using in their use of litter for urination. This helps avoid the delay in obtaining a sample needed by the veterinarian and avoids the related complications when the usual sample is not obtainable.

2. The litter of the invention is economically acceptable, e.g., low in cost.

3. The litter of the invention is an inert material and does not interfere in the interpretation of results of the urine analysis.

4. The litter material is easily used by untrained hospital staff, and clients (cat owners).

5. The litter material is easily dispensed in unit quantities measured in fluid ounces (volume), such as 2 ounce quantities in packages, such as package 10, or in containers containing a measured quantity (2 or 4 ounces) to clients for use at home for initial or follow-up physical examination procedures.

The material illustrated in FIGS. 1, 2, 7A and 7B consists of plastic granules or rubber granules or of coated granules approximately one to two millimeters in diameter, preferably consisting of reprocessed polyethylene or reprocessed polypropylene, which is black or dark brown in color and is extruded to provide a low density material.

The urine loss with the preferred material is minimal. Smaller size granules than one millimeter would have a greater surface area, and the amount of urine that would adhere to the granules would increase. Larger granules than five millimeters are not acceptable to cats. The size described herein is the most advantageous, but other sizes may be considered. This should not affect patent application.

THE METHOD OF THE INVENTION AT THE ANIMAL HOSPITAL OR AT THE HOME

When a urine sample is desired, the veterinarian quickly decides if the animal should be hospitalized. If hospitalized, a clean litter pan with about two ounces of the non-absorbent granules of the preferred type is placed in the cage with the cat. When the cat urinates, the urine is simply poured into a suitable container in preparation for urinalysis. Also, if used in the hospital, the granules may be washed and reused by the veterinarian to further reduce cost.

If the veterinarian decides to handle the case as an out-patient, a suitable amount of the granules is dispensed to the client with instructions to clean their present litter pan and place the granules in the pan. When the cat urinates the urine can be recovered and returned to the veterinarian for urinalysis.

FIG. 4 shows a first modification for the urine collecting system of the invention which imploys a novel tray 22 of generally rectangular construction and with long sides 28 and end sides 30 which has a center opening 24 fitted with a strainer 38 of circular shape in the sloping bottom of the tray 22. The sloping bottom walls 32 permit the urine in the center portion to collect above strainer 38 and as shown in the view of FIG. 4, the container 36 has an upper diameter of the opening to accommodate the circular periphery of the strainer whereby all of the urine collected passes into the container 36.

In this modification the special tray provided with sloping bottom walls is provided with a rim 26 to facilitate handling the tray, and a boss 34 is provided in order to connect the container 36 to the strainer portion in the central opening. To accommodate the height of the container, which is adapted to accept about 10-300 milliliters of urine, it is convenient to use either a 4 ounce or 8 ounce container, either plastic or paper. To adapt the container to its engagement within the boss there is provided a washer 40 as shown in FIG. 6 and the upper edge of the container 36 is provided with a thread projection 37 which fits into a corresponding recess of the boss 34 to thereby adapt the container unit 36 to be securely attached.

A support or stand 42 having a base 44, uprights 46, and a top frame 48 is provided at the sides of the tray 22 are provided to permit the attachment and detachment of the container after it has been filled. The litter granules which are of the preferred variety and are shown in FIGS. 7A and 7B are of circular cross-section prepared by cutting strands of extruded reprocessed polyolefin plastics, e.g., polypropylene, polyethylene, polybutadiene or the like. These plastics contain figment filler and have a density supply greater than one which makes them very easy to use, to decant urine therefrom, to wash, to dry, and to reuse.

A number of examples of the use of the novel litter 50 have been carried out in the inventor's home and in the inventor's hospital. In the inventor's home three cats, who were used to the ordinary clay litter, had the litter changed to that of the invention and 2-3 ounce quantities in the ordinary litter pan of the type in FIGS. 1 and 2 provided no difference in the normal urination behavior. The litter pans contained normal quantities of urine. The urine samples from each cat were collected and found to be clear, without any floating debris. In short, it is as representative as a sample taken from the bladder. It is much easier to collect than a catheter sample of urine.

In another example a cat suffering from a bladder infection was hospitalized for 48 hours. There was no passing or urine during this entire period of hospitalization. Attempts were made by the inventor to express the bladder manually. The cat resisted these attempts. It was then necessary to sedate the cat and take the sample of urine with a catheter. The cat was returned to the hospital for a checkup after treatment for the urinary infection had been completed over a 30 day period. The owner of the cat was given a cup of litter 50 and the owner put the litter into a pan at home that evening.

The next morning a sample of urine was obtained in accordance with the above method described in FIGS. 1 and 2. This sample procedure could not have occurred in the absence of the litter material of the invention since there was no way that the clay litter, which the owner had employed, could serve as a source from which the urine could be obtained.

The example which is given in the preceding paragraphs is that which uses litter 50 formed of extruded plastic, such as polyethylene or polypropylene. The pan in which this litter is used is that shown in FIGS. 1 and 2. It is within the contemplation of the invention to use coated granules of sand 161 illustrating a material other than plastic or rubber as litter 160. In this instance the coating 162 is about 2-3 mils thick and is of a urethene resin although any coating resin may be used. The container 36 may be used to hold litter 50 or litter 160.

Another example is the use of the litter 50 in an animal hospital in which the cats were put in cages over night and a pan supplied, such as a pan in FIGS. 1 and 2. During the first week of use in the animal hospital there were 12 units of 4 ounces each of litter 50 given to twelve owners of twelve cats for urine samples from each and the urine samples were obtained the next day or sooner.

The examples for the animal hospital use of four ounces represents the preferred amount of litter 50 which is spread in the tray or pan which the animal occupies in the hospital cage. Larger amounts up to eight ounces can be used but are wasteful. Generally there is a preference by the cat for the four ounce quantity since two ounce amounts which have been successfully used appear to engender reticence in the animal who exhibits a pattern of scratching and collecting of the litter in its activities.

Accordingly, in the preferred embodiment for dispensing the litter in packaged form, a container of four ounces capacity whether of the sealed cellophane bag type or of the plastic cup type may be employed. The preferred cup type which has been used in the hospital has identifying indicia for date, name, doctor and room which is helpful in the record keeping operation for a large animal hospital. The modification of FIGS. 4 through 6 illustrates a special purpose tray with a bottom having inwardly sloping sections of tetrahedral construction toward the center so that there is an automatic collection of urine by gravity at the center screen where a circular boss fits around a threaded portion at the base of the drain section to permit the threaded engagement of the urine collecting cup. The plastic container of four ounce capacity which serves to dispense litter and is provided with the cap bearing the indicia giving patient data can serve as the screw in the bottom urine container of four ounce capacity. This is the simplest, cheapest, most convenient and easily reuseable embodiment for urine collection that has been very successfully employed at the inventor's hospital.

In FIGS. 8 through 11, there is shown a second embodiment of a urine collecting device 60 which is comparable at its base to the inwardly sloping bottom construction of the first embodiment of tray 22 but which pours from the top. This second embodiment 60 includes a litter pan 62 having a generally rectangular form with rim 72, and has side walls 66, end walls 68 which are formed of the same unitary material of pan 62. A urine receptacle in this embodiment comprises a pan 64 having end walls 86, side walls 88, bottom wall 90 and a rim 92. The urine receptacle 64 shown in FIG. 9 underlies the entire pan 62, and the urine which collects at the sloping bottom walls 70 is stopped in its downward travel through drain fitting 78 by upper plug 80. If upper plug 80 is removed then the urine collects over the drain and would pass directly through the central opening 76 into the shallow urine pan 64. However, a lower plug 84 serves to hold the liquid so that upon its removal the liquid then passes through the drain fittings 78 having a wire screen or strainer 82, intermediate the upper plug 80 and the lower plug 84 which is formed of wire screen. The liquid which collects in the lower urine pan can be poured from a corner of a pan 64 as shown in FIG. 11 into the sample container 98.

This second embodiment illustrates a special receptacle designed to collect urine by the simple removal of the plugs 80 and 84 into the shallow pan illustrated by receptacle 64. The litter pan 62 rests over the urine receptacle pan 64 on the assembly illustrated in FIGS. 8, 9, 10 and 11. The litter pan 62 rests over the urine receptacle pans 64 supported by depending diagonal ribs 74 as seen in FIG. 8, which cooperate with complimentary notches 96 formed in the upstanding support ribs 94 shown in FIGS. 9 and 11. Ribs 74 and 94 are on heights adapted to support the top pan 62, e.g., litter pan, and a bottom pan 64, e.g., urine receptacle or pan in nesting relation.

Accordingly, the second embodiment represents a very low profile set of pans which can be used in special conditions where there is not a large amount of height available for the first embodiment of FIGS. 3 through 6.

In FIGS. 12 through 14 there is illustrated a third modification of the combination of litter pan and urine receptacle employing the novel litter 50 of the present invention. In this third embodiment the combination 100 comprises litter pan 102 and urine receptacle 104, each being generally rectangular in shape but provided with novel structural modifications in both the pan and urine receptacle to facilitate taking of urine sample. The litter pan 102 has end walls 106, side walls 108, and sloping bottom wall 110 which is of the same shallow slope as is the sloping bottom of the first and second modifications of the invention. The support for the bottom urine receptacle is provided by ribs 114 which are formed in the structure of the bottom receptacle so that the shoulder portions 115 serve to facilitate the stable supporting surface about the opening near top plug 120 which is the central opening for urine to pass into the urine receptacle 104.

The structure in FIG. 13 of the urine receptacle 102, end walls 126, bottom wall 130, rim 132, side walls 128 and top and bottom plugs 120 and 124 on upper and lower sides of strainer 122 is somewhat similar in the second embodiment of FIGS. 9 through 11. This third embodiment in FIG. 14 has the same purpose of the provision of a suitable urine catch basin as in the second embodiment but the receptacle 104 is smaller in area than that in the second embodiment of FIGS. 9 through 11.

This fourth embodiment in FIG. 15 is distinctive over all of the other novel embodiments of urine receptacle in the provision of a special pouring means to aid in handling urine collection in special situations. No pouring means as part of the pan is provided by the flat urine receptacle 104 of FIG. 14 in contrast to the special design of pouring spout 144 shown in FIGS. 15, 16 and 17. The pouring spout 144 comprises a strainer 146 which is constructed with horizontal leg 148 and depending leg 150 to depend from the vertical portion and connects at the top thereof a short distance from the top of the wall, the depending leg 150 having openings 152 which permit the urine to pass to the upper outlet of the spout 144 while holding the litter back. The special horizontal leg 148 and depending leg 150 are inserted into the corner of the litter pan 136 to effectively provide a combination of pouring means, straining means and litter pan in the same novel corner construction of the same pan which is used by the cat.

A variety of receptacles may be used with the novel litter pans. In FIG. 1 there the urine may be collected in a small sample within the empty flexible pouch 14 after using a conventional heat-sealing tool to reseal the sample for the hospital laboratory. Often the veterinarian must send out a sample to a special laboratory if he does not have an in-house laboratory to perform the analysis. For example, a slide* is more complicated than simple acidity testing. Analysis is needed from a remote laboratory. The in-house sample in pouch 14 is checked for simple components. The larger sample in receptacle 16 is sent out taking the urine in the cup 16 with lid 18, which can be sent in the mail to a remote laboratory or examined by a specialist in another city.

*A microscopic examination of a slide which has a urine sample to check cells, bacteria, etc.

The heat-sealed flexible package 14 which is resealed by conventional means is comprised of notches 134 which immobilize the pan 104 in its place on shoulders 115 and is retained by ribs 114 constituting a urine receptacle which is thereby immobilized below the special litter pan 100 to assure that all of the liquid sample will reach the receptacle 104 of FIG. 14.

The urine receptacle of FIG. 6 is an example of a urine receptacle 36 which threadedly engages the bottom of the tray 22 below the strainer 38.

THE CRITICAL PHYSICAL CHARACTERISTICS OF THE NOVEL LITTER 50 IN FIG. 7A AND LITTER 150 IN FIG. 7B OF THE INVENTION

It has been discovered that the novel litter of the invention is accepted by cats and members of the cat family while simultaneously aiding in obtaining a urine sample without the need for an overnight hospital stay, manual expressions or catheterization if the litter meets the critical requirements of being:

(1) non-absorbent
(2) non-porous (3) substantially smooth
(4) granular
(5) hydrophobic
(6) between about 1 and about 5 millimeters in particle size preferably about 1-2 millimeters for height, width and base.

Porous hydrophobic plastic and rubber materials have been disclosed in U.S. patent to Fisher, U.S. Pat. No. 3,765,371 but these are unsatisfactory since it is too difficult to squeeze urine from a stiff hard sponge.

Hydrophobic materials have been used, e.g., sand in Pallesi U.S. Pat. No. 3,752,120 but the urine is soaked into the sand and is retained to prevent an adequate quantity to be collected.

Obviously coated particles such as sand, which are 1-2 millimeters in size using a hydrophobic plastic or rubber coating may be used as litter 50 and reference numeral 160 designates the coated material in FIG. 7B.

It is surprising to discover that the cat or a member of the cat family finds the present litter compatible.

An illustrative example for the method which coats litter 160 is to:

(1) immerse the grains of sand which are from 1-2 millimeters in size after they have been washed and cleaned and dried, immersion being in a dilute solution (5-10%) of urethane resin in a solvent;

(2) removing the coated sand particles which are then dried in step 3 after the particles have been separated from each other and thereafter baked in step 4 to set the coating.

The method of immersion coating illustrated below is one of many conventional coating methods which may be employed to provide a 3 mil coating on the granules of 1-2 millimeter particle size. At 5% urethene resin solids in standard hydrocarbon solvents or in a hydrocarbon mixed with aliphatic ketone, acetone or methyl ethyl ketone (MEK), the coating by immersion is about 1-2 mils in thickness and 2 or 3 passes may be made through the immersion bath to build up the coating to a greater thickness. At 8-10% resin solids the thickness of the coating of about 3 mils. Both types of coating, single layer and multilayer, are contemplated. Frequently the second layer over the first layer helps in producing a smoother coating of the sand particles, litter 160 with coating 162 over sand 161.

The density of the coated sand particles 160 is far greater than the density of the extruded litter 50 and the lower density is preferred by the veterinarian. The lower density extruded material is easier to use in the animal hospital, particularly, with the novel pan structure which is adapted to handle the lower density extruded litter 50.

Finally, it is possible and may be under certain circumstances desirable to add perfumes, deodorizers, odor modification agents and other substances even those to repel insects if desired, these substances being well-known for such purposes without detracting from the spirit and scope of the discovery of the novel attributes of litter 50.

What is claimed is:

1. A urine collection system for cats and members of the cat family comprising a granular, non-absorbent, non-porous, hydrophobic litter which is capable of being spread in a pan, said litter having substantially cylindrical particles with a diameter between about 1 millimeter up to about 5 millimeters and a height between about 1 millimeter up to about 5 millimeters and being substantially smooth whereby the cat can urinate in the pan to permit easy removal of a urine sample at a minimum loss without the need to manually express the urine or catheterize the cat.

2. A urine collection system as claimed in claim 1 wherever said litter consists of extruded plastic cut into uniform size 1-2 millimeter diameter particles.

3. A system as claimed in claim 2 wherein said plastic is polypropylene which is pigmented in a dark color.

4. A system as claimed in claim 2 wherein said litter consists of extruded rubber.

5. A system as claimed in claim 1 wherein said litter is sand of particle size 1-2 millimeters in diameter and is coated with a hydrophobic coating selected from the group consisting of plastic and rubber and of particles coated with plastic or rubber.

6. A unitary package adapted for urine collection from a cat or a member of the cat family comprising:
a receptacle adapted to be used when empty to hold a sample of urine from said cat; and
granular, non-porous, hydrophobic substantially smooth litter in said receptacle in an amount of from 2 to 8 ounces by volume, said litter having substantially uniform particles with a diameter between about 1 millimeter up to about 5 millimeters and a height between about 1 millimeter up to about 5 millimeters between about 1 to about 5 millimeters in particle diameter, the packaged litter in said receptacle adapted to be used in a pan.

7. A package as claimed in claim 6 wherein said receptacle is a heat-sealed flexible plastic package adapted to hold said litter.

8. A package as claimed in claim 6 wherein said receptacle is a cup with a lid.

9. A package as claimed in claim 6 wherein said receptacle is an open pan.

10. A package as claimed in claim 6 wherein said receptacle comprises a cup, a lid for said cup and a heat-sealed package of litter which is contained in said cup.

11. In combination, a urine collection system for cats and members of the cat family, comprising:
a pan fitted with straining means;
a receptacle means adapted to be used to hold a sample of urine from said cat; and
granular, non-porous, hydrophobic substantially smooth litter in said receptacle in an amount of from 2 to 8 ounces by volume, said litter being of uniform particle size between about 1 to about 5 millimeters in particle diameter, the litter being placed in said receptacle means and being adapted to be used in said pan.

12. The combination claimed in claim 11 wherein said straining means is a strainer located at the center of said pan and is adapted to fill said receptacle means positioned there below.

13. The combination as claimed in claim 12 including means to retain said receptacle means below said strainer.

14. The combination as claimed in claim 11 wherein said receptacle means comprises a flat urine receptacle located below said straining means.

15. The combination as claimed in claim 11 wherein said receptacle means is a flat urine receptacle fitted with rim means and said pan with strainer means has its bottom fitted with retaining means to position said flat urine receptacle in urine receiving relation.

16. The combination as claimed in claim 11 wherein said receptacle means is part of said pan including said straining means and is located in a corner of said pan.

* * * * *